(12) United States Patent
Khoo et al.

(10) Patent No.: US 12,310,747 B2
(45) Date of Patent: May 27, 2025

(54) INTELLIGENT VASCULAR GRAFT

(71) Applicant: Hong Kong Centre for Cerebro-cardiovascular Health Engineering Limited, Hong Kong (HK)

(72) Inventors: Bee Luan Khoo, Hong Kong (HK); Zhiqiang Ma, Hong Kong (HK)

(73) Assignee: Hong Kong Centre for Cerebro-Cardiovascular Health Engineering Limited, Hong Kong (HK)

( * ) Notice: Subject to any disclaimer, the term of this patent is extended or adjusted under 35 U.S.C. 154(b) by 796 days.

(21) Appl. No.: 17/457,593

(22) Filed: Dec. 3, 2021

(65) Prior Publication Data
US 2023/0172537 A1    Jun. 8, 2023

(51) Int. Cl.
*A61B 5/00* (2006.01)
*A61B 5/0265* (2006.01)
(Continued)

(52) U.S. Cl.
CPC .......... *A61B 5/4851* (2013.01); *A61B 5/0265* (2013.01); *A61B 5/686* (2013.01);
(Continued)

(58) Field of Classification Search
CPC ..... A61B 5/4851; A61B 5/0265; A61B 5/686; A61B 5/02158; A61B 2562/0247;
(Continued)

(56) References Cited

U.S. PATENT DOCUMENTS 9,848,775 B2 * 12/2017 Tee .................. A61B 5/205
2003/0229388 A1 * 12/2003 Hayashi ............ A61B 5/02014
623/1.1

(Continued)

FOREIGN PATENT DOCUMENTS

WO    WO-0200118 A2 *   1/2002   ........... A61B 5/0031

OTHER PUBLICATIONS

Hertzman et. al. "Regional Differences in the Basal and Maximal Rates of Blood Flow in the Skin" (Year: 1948).*

(Continued)

*Primary Examiner* — Eric F Winakur
*Assistant Examiner* — Noah M Healy
(74) *Attorney, Agent, or Firm* — Knobbe Martens Olson & Bear LLP (57) ABSTRACT

A vascular graft includes a flexible substrate that can assume an unrolled configuration, in which the substrate extends along a main extension plane, and a rolled-up configuration, in which a first side of the substrate is facing radially inward and a second side of the substrate is facing radially outward. At least one pressure sensing device is arranged on the first side of the substrate and includes a first electrode, a second electrode, and a piezoelectric element arranged between the two electrodes. At least one velocity sensing device is (Continued)

arranged on the first side of the substrate and a first electrode, a second electrode, and a piezoelectric element arranged between the electrodes. The graft can be used in a vascular graft system.

22 Claims, 3 Drawing Sheets

(51) Int. Cl.
    *A61F 2/06*     (2013.01)
    *G16H 40/67*     (2018.01)
    *H10N 30/30*     (2023.01)
    *H10N 30/857*     (2023.01)

(52) U.S. Cl.
    CPC ............... *A61F 2/06* (2013.01); *G16H 40/67* (2018.01); *H10N 30/302* (2023.02); *H10N 30/306* (2023.02); *H10N 30/857* (2023.02)

(58) Field of Classification Search
    CPC . A61B 2562/028; A61B 5/026; A61B 5/6876; A61F 2/06; A61F 2002/077; H10N 30/857; H10N 30/306; H10N 30/302
    See application file for complete search history.

(56) References Cited

U.S. PATENT DOCUMENTS

| | | | |
|---|---|---|---|
| 2010/0094376 A1* | 4/2010 | Penner | A61N 1/0517 607/42 |
| 2010/0181871 A1* | 7/2010 | Daniel | H10N 30/306 73/579 |
| 2013/0053872 A1* | 2/2013 | Hansen | A61B 17/12031 606/151 |
| 2016/0331313 A1* | 11/2016 | Kuraguntla | A61B 5/02055 |

OTHER PUBLICATIONS

Loeb et. al. "Parylene as a Chronically Stable, Reproducible Microelectrode Insulator" (Year: 1977).*

Natta et. al. "Soft and flexible piezoelectric smart patch for vascular graft monitoring based on Aluminum Nitride thin film" (Year: 2019).*

* cited by examiner

INTELLIGENT VASCULAR GRAFT

FIELD OF THE INVENTION

The invention relates to a vascular graft.

BACKGROUND OF THE INVENTION

Vascular grafts are known. During a surgical procedure, a vascular graft comprising a shape of a hollow cylinder can be connected to two blood vessels such that after the vascular graft is connected to the two blood vessels, the blood flow from one of the two blood vessels is directed through the vascular graft and from the vascular graft to the other one of the two blood vessels. It is generally desirable to obtain reliable information about the condition of the flow paths along which blood flows in an easy manner, particularly after a vascular graft has been implanted.

SUMMARY OF THE INVENTION

An object of the invention is to provide a solution to obtain reliable information about the condition of the flow paths along which blood flows in an easy manner, particularly after a vascular graft has been implanted.

According to a first aspect of the present invention, the object is solved by a vascular graft comprising the features of claim 1. The vascular graft comprises a flexible substrate. The flexible substrate can assume an unrolled configuration, in which the substrate extends along a main extension plane, and a rolled-up configuration, in which a first surface of the substrate on a first side of the substrate is facing radially inward and a second surface of the substrate on a second side of the substrate is facing radially outward. The vascular graft further comprises at least one pressure sensing device. The at least one pressure sensing device is arranged on the first side of the substrate and comprises a first electrode, a second electrode, and a piezoelectric element arranged between the first electrode and the second electrode. The vascular graft further comprises at least one velocity sensing device. The at least one velocity sensing device is arranged on the first side of the substrate and comprises a first electrode, a second electrode, and a piezoelectric element arranged between the first electrode and the second electrode.

The vascular graft comprises the flexible substrate. The flexibility of the substrate ensures that the substrate can assume an unrolled configuration and a rolled-up configuration and can transfer from the unrolled configuration to the rolled-up configuration and from the rolled-up configuration to the unrolled configuration.

The flexible substrate can assume the unrolled configuration, in which the substrate extends along the main extension plane, and the rolled-up configuration, in which the first surface of the substrate on the first side of the substrate is facing radially inward and the second surface of the substrate on the second side of the substrate is facing radially outward. Particularly, during a surgical procedure, the vascular graft can be provided in the unrolled configuration and can be brought into the rolled-up configuration to be connected to two blood vessels such that after the vascular graft is connected to the two blood vessels, the blood flow from one of the two blood vessels is directed through the vascular graft and from the vascular graft to the other one of the two blood vessels. The unrolled configuration ensures that the vascular graft can be transported in a space saving way, particularly if the vascular graft is transported together with other vascular grafts, which are also in the unrolled configuration. Preferably, the flexible substrate assuming the unrolled configuration is the same as the vascular graft assuming the unrolled configuration. Similarly, it is preferred that the flexible substrate assuming the rolled-up configuration is the same as the vascular graft assuming the rolled-up configuration. Since in the rolled-up configuration, the first surface of the substrate is facing radially inward, the blood flows along the first surface. For example, the blood flows along an axial direction of the substrate in the rolled-up configuration.

The vascular graft further comprises the at least one pressure sensing device. Each pressure sensing device is preferably adapted to provide signals which comprise information from which the pressure of the blood, particularly the static pressure of the blood, can be inferred. The vascular graft may comprise one pressure sensing device or multiple pressure sensing devices. The features, technical effects and/or advantages described in connection with one pressure sensing device also apply to each of the pressure sensing devices at least in an analogous manner, so that no corresponding repetition is made here.

The at least one pressure sensing device is arranged on the first side of the substrate and comprises the first electrode, the second electrode, and the piezoelectric element arranged between the first electrode and the second electrode. Since the at least one pressure sensing device is arranged on the first side of the substrate, the at least one pressure sensing device is facing radially inward on the side of the substrate facing the blood flow through the vascular graft. Depending on the pressure of the blood, particularly the static pressure of the blood, the blood arranged inside the vascular graft applies a particular mechanical load onto each of the pressure sensing devices. The applied mechanical load onto a particular pressure sensing device implies that a mechanical stress is applied to the piezoelectric element of the pressure sensing device and the mechanical stress applied to the piezoelectric element results in a variation of the electric field extending between the surfaces of the piezoelectric element. From the electric field extending between the surfaces of the piezoelectric element the pressure of the blood can be inferred. Preferably, each surface of the piezoelectric element extends in parallel to the main extension plane. Preferably, one of the surfaces of the piezoelectric element is attached to a surface of the first electrode of the pressure sensing device. Preferably, the other one of the surfaces of the piezoelectric element is attached to a surface of the second electrode of the pressure sensing device. The pressure of the blood may vary over time due to the heart muscle pumping blood through the vascular graft. For each point in time, depending on the current pressure of the blood, particularly the static pressure of the blood, the blood applies a particular mechanical load onto each of the pressure sensing devices.

The vascular graft further comprises the at least one velocity sensing device. Each velocity sensing device is preferably adapted to provide signals which comprise information from which the velocity of the blood can be inferred. The vascular graft may comprise one velocity sensing device or multiple velocity sensing devices. The features, technical effects and/or advantages described in connection with one velocity sensing device also apply to each of the velocity sensing devices at least in an analogous manner, so that no corresponding repetition is made here.

The at least one velocity sensing device is arranged on the first side of the substrate and comprises the first electrode, the second electrode, and the piezoelectric element arranged between the first electrode and the second electrode. Since the at least one velocity sensing device is arranged on the first side of the substrate, the at least one velocity sensing device is facing radially inward on the side of the substrate facing the blood flow through the vascular graft. Depending on the velocity of the blood, the blood applies a particular mechanical load onto each of the velocity sensing devices. The applied mechanical load onto a particular velocity sensing device implies that a mechanical stress is applied to the piezoelectric element of the velocity sensing devices and the mechanical stress applied to the piezoelectric element results in a variation of the electric field extending between the surfaces of the piezoelectric element. From the electric field extending between the surfaces of the piezoelectric element the velocity of the blood can be inferred. Preferably, each surface of the piezoelectric element extends in parallel to the main extension plane. Preferably, one of the surfaces of the piezoelectric element is attached to a surface of the first electrode of the velocity sensing device. Preferably, the other one of the surfaces of the piezoelectric element is attached to a surface of the second electrode of the velocity sensing device. The velocity of the blood may vary over time due to the heart muscle pumping blood through the vascular graft. For each point in time, depending on the current velocity of the blood, particularly depending on the current difference between the velocity of the blood at a radially inner side and the velocity of the blood at a radially outer side, the blood applies a particular mechanical load onto each of the velocity sensing devices.

Therefore, the vascular graft is adapted to provide information from which the pressure and the velocity of the blood can be determined, particularly at certain positions in the vascular graft at which the pressure and velocity sensing devices are arranged. For example, information about the cross section available for the blood to flow through the vascular graft can be derived from the pressure and the velocity of the blood at certain positions in the vascular graft. For example, the location, size, and morphology (e.g., shape of a triangle, semi-circle, or rectangle) of a thrombus arranged radially inward of the first surface can be derived.

In summary, the vascular graft allows to obtain reliable information about the condition of the flow paths along which blood flows in an easy manner, particularly after the vascular graft has been implanted.

According to a preferred embodiment of the vascular graft, the substrate comprises in the unrolled configuration a rectangular shape and in the rolled-up configuration a cylindrical shape, preferably the shape of a hollow cylinder. The rectangular shape allows the vascular graft to be manufactured together with other vascular grafts on a single wafer in a resource-efficient and material-saving manner. The cylindrical shape may depart from a perfect cylindrical shape in such a way that the shape of substrate comprises sections arranged one next to the other along the direction of blood flow, wherein each section comprises a cylindrical shape. Particularly, the cylindrical shape also includes any shapes the substrate may assume while being connected to two blood vessels.

According to a preferred embodiment of the vascular graft, the substrate comprises Polydimethylsiloxane, PDMS. The substrate may be made of PDMS. PDMS provides a material that ensures a flexibility of the substrate which is similar to the flexibility of blood vessels such that the mechanical properties of a vascular graft with a substrate comprising PDMS is particularly compatible with the mechanical properties of blood vessels.

According to a preferred embodiment of the vascular graft, each pressure sensing device is formed of a layer stack comprising multiple layers, wherein, when the substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode. In case each pressure sensing device is formed of a layer stack comprising multiple layers, each layer of the pressure sensing device can be manufactured with techniques known to manufacture layers for microelectromechanical systems. In case each layer extends in parallel to the main extension plane, the layers can be manufactured one after the other with techniques known to manufacture layers for microelectromechanical systems, which provides a vascular graft that can be manufactured in a time efficient manner. Further, in case the vascular graft comprises multiple pressure sensing devices, the layers of the pressures sensing devices can be manufactured in parallel, which provides a vascular graft that can be manufactured in a time efficient manner.

According to a preferred embodiment of the vascular graft, a fourth layer of the layer stack comprises a flexible layer arranged between the substrate and the first electrode. The flexibility of the flexible layer ensures that the flexible layer can assumed a deformed configuration, particularly if the substrate assumes the rolled-up configuration, and can reduce the deformation of the first electrode in the rolled-up configuration reducing the mechanical load on the first electrode, which increases the service life of the vascular graft.

According to a preferred embodiment of the vascular graft, each pressure sensing device comprises in the unrolled configuration a rectangular shape, the rectangular shape comprises preferably an extension along a first direction parallel to the main extension plane of 0.2 to 1.5 mm, preferably 1 mm, and an extension along a second direction parallel to the main extension plane and perpendicular to the first direction of 0.2 to 1 mm, preferably 0.5 mm. The rectangular shape allows each pressure sensing device to be manufactured with the assistance of techniques to manufacture microelectromechanical systems (MEMS), including known structuring steps.

According to a preferred embodiment of the vascular graft, each pressure sensing device is adapted to detect pressures from 0 to 40 kPa. Preferably, each pressure sensing device is adapted detect blood pressures of 0 kPa, 40 kPa, and each value between 0 kPa and 40 kPa.

According to a preferred embodiment of the vascular graft, each velocity sensing device comprises a cantilever, which comprises the piezoelectric element of the respective velocity sensing device. Depending on the velocity of the blood, the blood applies a particular mechanical load onto the cantilever. The applied mechanical load onto the cantilever implies that a mechanical stress is applied to the piezoelectric element of the velocity sensing device and the mechanical stress applied to the piezoelectric element results in a variation of the electric field extending between the surfaces of the piezoelectric element. Preferably, each cantilever is surrounded by blood from a radially inner side and a radially outer side. It is preferred that due to the blood flow through the vascular graft, the velocity of the blood at the radially inner side of the cantilever may be higher than the velocity of the blood at the radially outer side of the cantilever, or, alternatively, the velocity of the blood at the radially inner side of the cantilever may be lower than the velocity of the blood at the radially outer side of the cantilever. Therefore, the static pressure of the blood at the radially outer side of the cantilever may be higher than the static pressure of the blood at the radially inner side of the cantilever. Alternatively, the static pressure of the blood at the radially outer side of the cantilever may be lower than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. Alternatively, the cantilever may bend towards the radially outer side of the cantilever in case the velocity of the blood at the radially inner side of the cantilever is lower than the velocity of the blood at the radially outer side of the cantilever. The velocity of the blood may vary over time due to the heart muscle pumping blood through the vascular graft. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices, particularly on each of the cantilevers.

According to a preferred embodiment of the vascular graft, in the unrolled configuration, the cantilever extends from a supported end in parallel to the main extension plane towards a free end such that, in the rolled-up configuration, the free end is positioned radially inward of a portion of a wall defining a recess formed in the flexible substrate, wherein the recess is open towards the first side of the substrate. Preferably, each pair of cantilever and recess is adapted such that blood can enter the recess. Therefore, each cantilever may be surrounded by blood from a radially inner side of the cantilever and a radially outer side of the cantilever. Due to the blood flow through the vascular graft and the recess, the velocity of the blood at the radially inner side of the cantilever may be higher than the velocity of the blood at the radially outer side of the cantilever, e.g., the velocity of the blood in the recess. Therefore, the static pressure of the blood at the radially outer side of the cantilever may be higher than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. The velocity of the blood may vary over time due to the heart muscle pumping blood through the vascular graft. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices, particularly on each of the cantilevers.

According to a preferred embodiment of the vascular graft, each velocity sensing device is formed of a layer stack comprising multiple layers, wherein, when the substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode. In case each velocity sensing device is formed of a layer stack comprising multiple layers, each layer of the velocity sensing device can be manufactured with techniques known to manufacture layers for microelectromechanical systems. In case each layer extends in parallel to the main extension plane, the layers can be manufactured one after the other with techniques known to manufacture layers for microelectromechanical systems, which provides a vascular graft that can be manufactured in a time efficient manner. Further, in case the vascular graft comprises multiple velocity sensing devices, the layers of the velocity sensing devices can be manufactured in parallel, which provides a vascular graft that can be manufactured in a time efficient manner. Further, in case the vascular graft comprises multiple pressure sensing devices and multiple velocity sensing devices, the layers of the pressure sensing devices and the layers of the velocity sensing devices can be manufactured in parallel, which provides a vascular graft that can be manufactured in a very time efficient manner.

According to a preferred embodiment of the vascular graft, a fourth layer of the layer stack comprises a flexible layer arranged between the substrate and the first electrode. The flexibility of the flexible layer ensures that the flexible layer can assumed a deformed configuration, particularly if the substrate assumes the rolled-up configuration, and can reduce the deformation of the first electrode in the rolled-up configuration reducing the mechanical load on the first electrode, which increases the service life of the vascular graft.

According to a preferred embodiment of the vascular graft, the recess comprises in the unrolled configuration a shape of a rectangular cuboid, the rectangular cuboid comprises preferably an extension along a first direction parallel to the main extension plane of 0.5 to 1.5 mm, preferably 1 mm, an extension along a second direction parallel to the main extension plane and perpendicular to the first direction of 0.5 to 1 mm, preferably 0.8 mm, and an extension along a third direction perpendicular to the main extension plane of 0.2 to 1 mm, preferably 0.5 mm. The shape of a rectangular cuboid allows each velocity sensing device to be manufactured with the assistance of techniques to manufacture microelectromechanical systems (MEMS), including known structuring steps.

According to a preferred embodiment of the vascular graft, each velocity sensing device comprises in the unrolled configuration a square shape, the square shape comprises preferably an extension along a first direction parallel to the main extension plane of 0.2 to 1.5 mm, preferably 0.5 mm, and an extension along a second direction parallel to the main extension plane and perpendicular to the first direction of 0.2 to 1.5 mm, preferably 0.5 mm. The square shape allows each velocity sensing device to be manufactured with the assistance of techniques to manufacture microelectromechanical systems (MEMS), including known structuring steps.

According to a preferred embodiment of the vascular graft, each velocity sensing device is adapted to detect flow velocities from 0 to 1000 ml/min. Preferably, each velocity sensing device is adapted detect blood flow velocities of 0 ml/min, 1000 ml/min, and each value between 0 ml/min and 1000 ml/min.

According to a preferred embodiment of the vascular graft, the piezoelectric element of the pressure sensing device comprises polyvinylidene difluoride, PVDF, and/or the piezoelectric element of the velocity sensing device comprises polyvinylidene difluoride, PVDF. Each piezoelectric element may be made of PVDF. PVDF provides a material that allows to use piezoelectricity to detect pressures and velocities of blood with a vascular graft.

According to a preferred embodiment of the vascular graft, the thickness of the piezoelectric element of the pressure sensing device and/or the thickness of the piezoelectric element of the velocity sensing device perpendicular to the main extension plane is 2 to 20 μm, preferably 4 μm. The thickness of the piezoelectric element of the pressure sensing device and/or the thickness of the piezoelectric element of the velocity sensing device perpendicular to the main extension plane is 2 to 20 μm, preferably 4 μm, resulted in particularly precise measurements of the pressures and velocities of the blood.

According to a preferred embodiment of the vascular graft, the flexible layer of the pressure sensing device comprises polyimide, PI, and/or the flexible layer of the velocity sensing device comprises polyimide, PI. Each flexible layer may be made of PI. PI provides a material that resulted in a particularly strong bond to the substrate and to the first electrode and resulted in a particular increase in service life of the vascular graft.

According to a preferred embodiment of the vascular graft, wherein the thickness of the flexible layer of the pressure sensing device and/or the thickness of the flexible layer of the velocity sensing device perpendicular to the main extension plane is 2 to 25 μm, preferably 8 μm. A thickness of the flexible layer of the pressure sensing device and/or a thickness of the flexible layer of the velocity sensing device perpendicular to the main extension plane is 2 to 25 μm, preferably 8 μm, resulted in a particularly long service life of the vascular graft.

According to a preferred embodiment of the vascular graft, wherein each pressure sensing device and each velocity sensing device are arranged on the first side of the substrate such that, in the rolled-up configuration, the pressure sensing and velocity sensing devices are arranged along a line, preferably with a distance between the devices along the line of 1 to 10 mm, particularly preferred 5 mm, wherein the line extends along an axial direction of the substrate and is parallel to the axis around which the substrate is rolled up in the rolled-up configuration. In case the pressure sensing and velocity sensing devices are arranged along the line, which extends along the axial direction of the substrate allows to detect pressures and velocities at different positions along the axial direction of the substrate.

According to a preferred embodiment of the vascular graft, the vascular graft further comprises electrically conductive paths, wherein each of the paths is coupled with one end, e.g., a first end, to one of the elements comprising the first electrode of the pressure sensing device, the second electrode of the pressure sensing device, the first electrode of the velocity sensing device, and the second electrode of the velocity sensing device, wherein each of the paths extends in a meandering shape from the respective first end to a respective second end. The meandering shape of each of the electrically conductive paths allows to employ electrically conductive materials as materials to form the electrically conductive paths, such as metals, and still allow the vascular graft to be flexible enough to assume the rolled-up configuration from the unrolled configuration.

According to a preferred embodiment of the vascular graft, the vascular graft further comprises a flexible encapsulation layer, which is arranged on the first side of the substrate such that, in the rolled-up configuration, the flexible encapsulation layer is arranged radially inward of each of the pressure sensing devices, each of the velocity sensing devices, and/or each of the electrically conductive paths. The encapsulation layer may provide a protection of each of the pressure sensing devices, each of the velocity sensing devices, and/or each of the electrically conductive paths against blood and/or water. Further, the encapsulation layer may provide an electrical insulation of each of the pressure sensing devices, each of the velocity sensing devices, and/or each of the electrically conductive paths against blood and/or water.

According to a preferred embodiment of the vascular graft, the encapsulation layer comprises parylene, preferably a chlorinated parylene, particularly preferred parylene C. The encapsulation layer may be made of parylene, preferably a chlorinated parylene, particularly preferred parylene C. Parylene, preferably a chlorinated parylene, particularly preferred parylene C, provides a material that resulted in a particularly strong bond to each of the pressure sensing devices, particularly to each of the second electrode of the pressure sensing devices, to each of the velocity sensing devices, particularly to each of the second electrode of the velocity sensing devices, and/or to each of the electrically conductive paths.

According to a preferred embodiment of the vascular graft, wherein the thickness of the encapsulation layer perpendicular to the main extension plane is 1 to 10 μm, preferably 5 μm. A thickness of the encapsulation layer perpendicular to the main extension plane of 1 to 10 μm, preferably 5 μm, resulted in a particularly long service life of the vascular graft.

According to a second aspect of the present invention, the object is solved by a vascular graft system comprising the features of claim 22. The vascular graft system comprises a vascular graft according to an embodiment of the first aspect of the present invention and a flexible processing unit configured to be attachable to a skin and configured to process signals received from the vascular graft. The flexible processing unit may be connected via leads to lead pads. Each lead pad may be coupled to a second end of a respective electrically conductive path. The flexible processing unit is preferably configured to process signals received from the vascular graft via the leads. The flexible processing unit may be attached to the skin of a patient. The flexible processing unit may be adapted to send signals via a wireless interface to a user device with a display on which the user can view information derived from signals provided by each of the pressure sensing devices and by each of the velocity sensing devices and processed by the flexible processing unit. The flexible processing unit may comprise a charge amplifier, a filter, a signal processor, and a wireless module. The flexible processing unit may be adapted to process the signals it receives from the lead pads and is adapted to generate signals that comprise information from which the pressure of the blood, particularly the static pressure of the blood, which applies the mechanical load onto a respective pressure sensing device, can be inferred. Further, the flexible processing unit may be adapted to send the generated signals via the wireless interface to the user device. The patient can then view information relating to the pressure of the blood, particularly the static pressure of the blood, displayed on the display. Further, the flexible processing unit may be adapted to generate signals that comprise information from which the velocity of the blood, particularly the difference between the velocity of the blood at the radially inner side of the cantilever and the velocity of the blood at the radially outer side of the cantilever, due to which a particular mechanical load is applied to the respective velocity sensing device, can be inferred. Further, the flexible processing unit may be adapted to send the generated signals via the wireless interface to the user device. The patient can then view information relating to the velocity of the blood, particularly the difference between the velocity of the blood at the radially inner side of the cantilever and the velocity of the blood at the radially outer side of the cantilever, displayed on the display. The features, technical effects and/or advantages described in connection with the first aspect of the present invention also apply to the second aspect of the present invention at least in an analogous manner, so that no corresponding repetition is made here.

The vascular graft can be manufactured according to a method of manufacturing the vascular graft described as follows. The method may comprise eight steps (steps (a) to (h)). Particularly, the vascular graft may be manufactured with the assistance of techniques to manufacture microelectromechanical systems (MEMS). In step (a), a single-polished silicon wafer may be cleaned with acetone and/or ethyl alcohol. In step (b), Polyimide (PI) may be spin-coated on the silicon wafer and may be heated in a hot oven at 280° C. for 10 min to form a PI film. In step (c), a sputter-coating Au/Cr (160/40 nm) layer may be deposited onto the PI film through a shadow mask. In step (d), a piezoelectric PVDF layer may be fabricated. The fabrication of the PVDF layer may comprise dissolving PVDF powder in dimethylformamide with a weight fraction of, e.g., 15 wt. % (weight percent). The fabrication of the PVDF layer may further comprise exposing the surface of the PI layer fabricated in step (b) and the surface of the Au/Cr layer on the PI layer fabricated in step (c) to oxygen plasma for 60 s before spin-coating of PVDF to increase the interfacial adhesion both between the PI layer and the PVDF layer and between the Au/Cr layer and the PVDF layer. After spin-coating, the PVDF film may be heated using a hot plate at 30° C. for 30 min and may then be annealed at 100° C. for 2 h with a vacuum drying oven to improve the β-phase crystallinity. In step (e), a sputter-coating Au/Cr (160/40 nm) layer may be deposited onto the PVDF layer through a shadow mask. In step (f), the layers deposited on top of the silicon wafer may be patterned by a reactive ion etching, RIE, process during which a layer of positive photoresist may be employed as a mask. In step (g), water-soluble tapes, WSTs, may be used as stamps to pick up the patterned layers. In step (h), a flexible Polydimethylsiloxane, PDMS, substrate may be fabricated by a PDMS molding process. Negative molds of the required size of the substrate may be fabricated by a rapid prototyping process. The PDMS substrate may be peeled out of the molds after PDMS casting. The PDMS substrate may then bonded to the patterned layers. PDMS substrate and the WST may be exposed to UV-induced ozone, which creates chemical groups between the patterned layers and the PDMS substrate to enhance bonding strength. The patterned layers may be attached to the PDMS substrate and the WST, the patterned layers, and the PDMS substrate may be heated in an oven at 70° C. for 10 min, which formed strong bonding between the PDMS substrate and the patterned layers. The WST, the patterned layers, and the PDMS substrate may be immersed in water to remove WSTs. An encapsulation layer may be formed on top of the patterned layers and the PDMS. A uniform encapsulation layer may be formed by employing a vacuum evaporator and a 5 μm thick parylene C encapsulation layer may be formed to provide a protection against blood and water and an electrical insulation. A dilute isopropyl alcohol-water solution of organic silane gamma-methacryloxypropyltrimethoxysilane may be used before parylene C deposition to improve the adhesion significantly. After the deposition of the encapsulation layer, the vascular graft may be put on a hot plate at 100° C., and a voltage of 60 V/μm may be applied to the lead pads to polarize the piezoelectric PVDF elements 19. After polarization treatment, the lead pads may be short-circuited for 24 h.

BRIEF DESCRIPTION OF THE DRAWINGS

Further features, advantages and application possibilities of the present invention may be derived from the following description of exemplary embodiments and/or the figures. Thereby, all described and/or visually depicted features for themselves and/or in any combination may form an advantageous subject matter and/or features of the present invention independent of their combination in the individual claims or their dependencies. Furthermore, in the figures, same reference signs may indicate same or similar objects.

FIG. 1 (a) schematically illustrates an embodiment of a vascular graft in an unrolled configuration according to the present invention, FIG. 1 (b) a sectional view along the line A-A' in FIG. 1 (a)

DETAILED DESCRIPTION OF THE PREFERRED EMBODIMENTS

FIG. 1 schematically illustrates an embodiment of a vascular graft 1 according to the present invention. The vascular graft 1 comprises a flexible substrate 3, two pressure sensing devices 5, two velocity sensing devices 7, and electrically conductive paths 9.

Figure 1A:
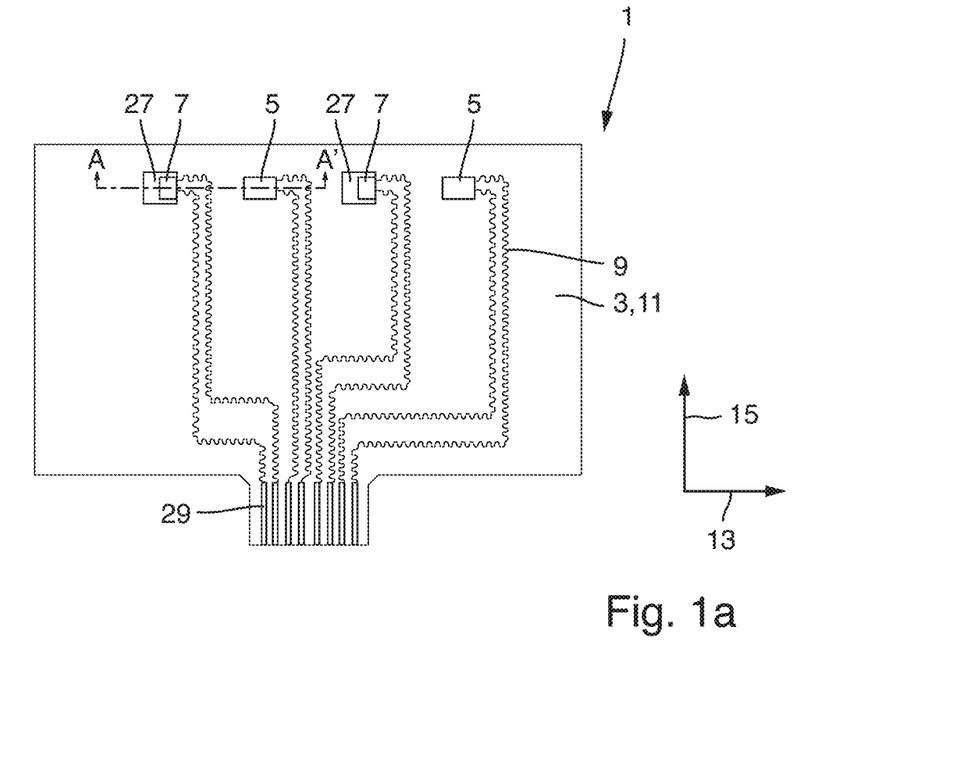

The flexible substrate 3 can assume an unrolled configuration, in which the substrate extends along a main extension plane. The unrolled configuration is shown in FIG. 1. FIG. 1 (a) is a view onto a first surface 11 of the substrate 3 on a first side of the substrate 3. The two pressure sensing devices 5 and the two velocity sensing devices 7 are arranged on the first side of the substrate 3. The substrate 3 comprises in the unrolled configuration shown in FIG. 1 (a) a rectangular shape, which is visible in the view perpendicular to the main extension plane and onto the first surface 11 in FIG. 1 (a). The substrate 3 comprises Polydimethylsiloxane, PDMS.

Each pressure sensing device 5 comprises in the unrolled configuration shown in FIG. 1 a rectangular shape. The rectangular shape comprises an extension along a first direction 13 parallel to the main extension plane of 0.2 to 1.5 mm, preferably 1 mm, and an extension along a second direction 15 parallel to the main extension plane and perpendicular to the first direction 13 of 0.2 to 1 mm, preferably 0.5 mm. Each pressure sensing device 5 is adapted to detect pressures from 0 to 40 kPa. Each velocity sensing device 7 comprises in the unrolled configuration shown in FIG. 1 a square shape. The square shape comprises an extension along the first direction 13 of 0.2 to 1.5 mm, preferably 0.5 mm, and an extension along the second direction 15 of 0.2 to 1.5 mm, preferably 0.5 mm. Each velocity sensing device 7 is adapted to detect flow velocities from 0 to 1000 ml/min.

Figure 1B:
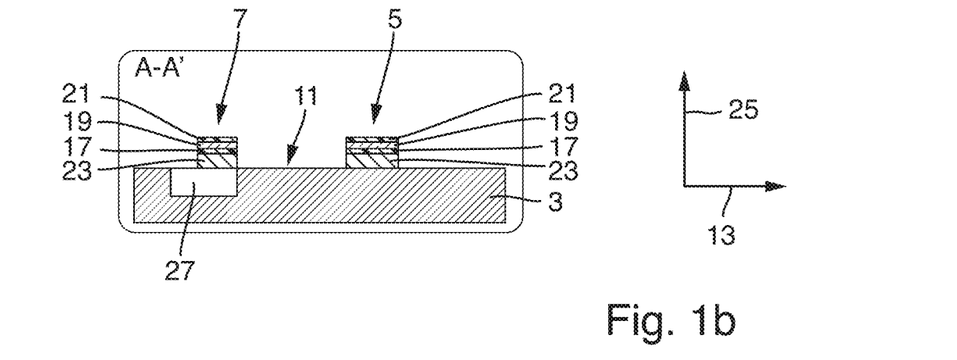

FIG. 1 (b) is a sectional view along the line A-A' in FIG. 1 (a). FIG. 1 (b) shows one pressure sensing device 5 and one velocity sensing device 7. The paths 9 are not displayed in FIG. 1 (b). The pressure sensing device 5 and the velocity sensing device 7 shown in FIG. 1 (b) are shown as examples and each pressure sensing device 5 of the vascular graft 1 and each velocity sensing device 7 of the vascular graft 1 are configured in a similar manner as the configuration of the pressure sensing device 5 and the velocity sensing device 7 shown in FIG. 1 (*b*), respectively.

The pressure sensing device 5 comprises multiple layers. In the unrolled configuration as shown in FIG. 1, each layer extends in parallel to the main extension plane, i.e., along the first direction 13 and along the second direction 15. A first layer of the multiple layers comprises a first electrode 17, a second layer of the multiple layers comprises a piezoelectric element 19, a third layer of the multiple layers comprises a second electrode 21, and a fourth layer of the layer stack comprises a flexible layer 23. The flexible layer 23 is arranged between the substrate 3 and the first electrode 17 and the piezoelectric element 19 is arranged between the first electrode 17 and the second electrode 21. The thickness of the piezoelectric element 19 perpendicular to the main extension plane, i.e., along a third direction 25 perpendicular to the first direction 13 and perpendicular to the second direction 15, is 2 to 20 µm, preferably 4 µm. The thickness of the flexible layer 23 along the third direction 25 is 2 to 25 µm, preferably 8 µm. The first electrode 17 and the second electrode 21 each comprise gold, Au, and chromium, Cr. The piezoelectric element 19 comprises polyvinylidene difluoride, PVDF, and the flexible layer 23 comprises polyimide, PI.

Similarly, the velocity sensing device 7 comprises multiple layers. In the unrolled configuration as shown in FIG. 1, each layer extends in parallel to the main extension plane. A first layer of the multiple layers comprises a first electrode 17, a second layer of the multiple layers comprises a piezoelectric element 19, a third layer of the multiple layers comprises a second electrode 21, and a fourth layer of the layer stack comprises a flexible layer 23. The flexible layer 23 is arranged between the substrate 3 and the first electrode 17 and the piezoelectric element 19 is arranged between the first electrode 17 and the second electrode 21. The thickness of the piezoelectric element 19 perpendicular to the main extension plane is 2 to 20 µm, preferably 4 µm. The thickness of the flexible layer 23 along the third direction 25 is 2 to 25 µm, preferably 8 µm. The first electrode 17 and the second electrode 21 each comprise gold, Au, and chromium, Cr. The piezoelectric element 19 comprises polyvinylidene difluoride, PVDF, and the flexible layer 23 comprises polyimide, PI.

The velocity sensing device 7 comprises a cantilever, which comprises the first electrode 17, the piezoelectric element 19, the second electrode 21, and the flexible layer 23 of the velocity sensing device 7. The cantilever extends from a supported end in parallel to the main extension plane towards a free end. The free end is arranged on the first side of the substrate 3 above a portion of a wall, preferably above a portion of a bottom wall, defining a recess 27, which is open towards the first side of the substrate 3. The recess 27 comprises in the unrolled configuration as shown in FIG. 1 a shape of a rectangular cuboid. The rectangular cuboid comprises an extension along the first direction 13 of 0.5 to 1.5 mm, preferably 1 mm, an extension along the second direction 15 of 0.5 to 1 mm, preferably 0.8 mm, and an extension along the third direction 25 of 0.2 to 1 mm, preferably 0.5 mm.

FIG. 1 (*a*) displays eight paths 9. A first path is coupled with one end to the first electrode 17 of the pressure sensing device 5 shown in the figure on the left. A second path is coupled with one end to the second electrode 21 of the pressure sensing device 5 shown in the figure on the left. A third path is coupled with one end to the first electrode 17 of the pressure sensing device 5 shown in the figure on the right. A fourth path is coupled with one end to the second electrode 21 of the pressure sensing device 5 shown in the figure on the right. A fifth path is coupled with one end to the first electrode 17 of the velocity sensing device 7 shown in the figure on the left. A sixth path is coupled with one end to the second electrode 21 of the velocity sensing device 7 shown in the figure on the left. A seventh path is coupled with one end to the first electrode 17 of the velocity sensing device 7 shown in the figure on the right. An eighth path is coupled with one end to the second electrode 21 of the velocity sensing device 7 shown in the figure on the right. Each of the paths 9 extends in a meandering shape from the respective first end to a respective second end. Each second end is coupled to a respective lead pad 29. Each lead pad 29 extends along the second direction 15 and forms a lead pad 29 of a number of lead pads, which are arranged parallel to each other.

Figure 2:
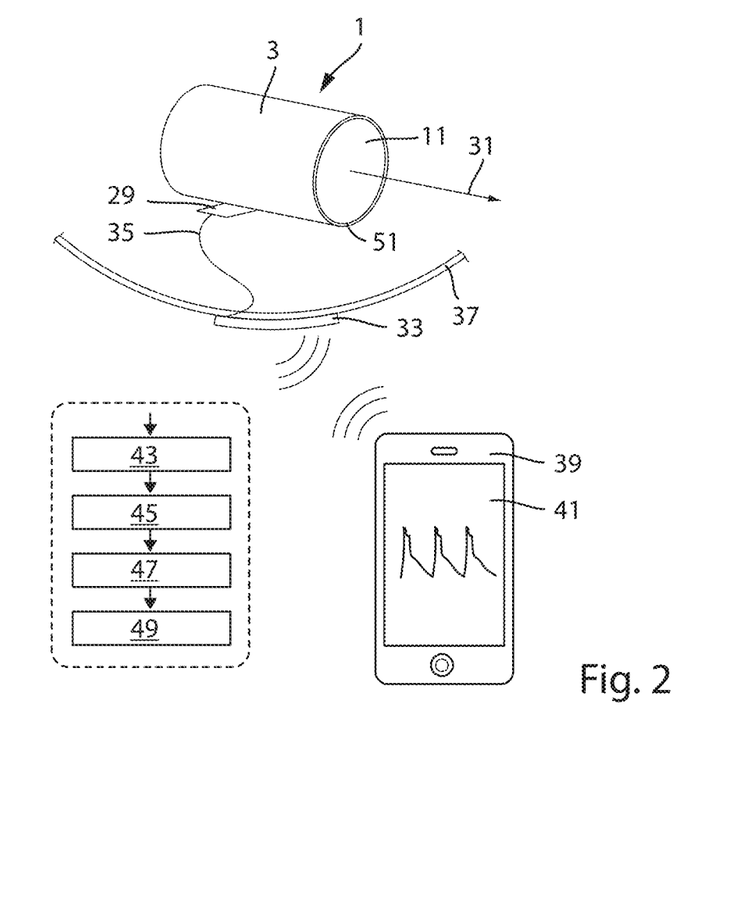
FIG. 2 schematically illustrates the embodiment of the vascular graft of FIG. 1 in a rolled-up configuration, FIG. 3 schematically illustrates a portion of the embodiment of the vascular graft of FIGS. 1 and 2, and FIG. 4 schematically illustrates a method of manufacturing the vascular graft of FIGS. 1 to 3.

FIG. 2 schematically illustrates the embodiment of the vascular graft 1 of FIG. 1 in a rolled-up configuration. The first surface 11 of the substrate 3 on the first side of the substrate 3 is facing radially inward and a second surface of the substrate 3 on a second side of the substrate 3 is facing radially outward. The substrate 3 comprises the shape of a hollow cylinder, which defines an axial direction 31. The two pressure sensing devices 5 and the two velocity sensing devices 7 are arranged on the first side of the substrate 3 such that, in the rolled-up configuration shown in FIG. 2, the two pressure sensing devices 5 and the two velocity sensing devices 7 are arranged along a line with a distance between the devices along the line of 1 to 10 mm, particularly preferred 5 mm. The line extends along the axial direction 31 of the substrate 3 in the rolled-up configuration. The free ends of the velocity sensing devices 7 are positioned radially inward of the respective portion of the wall defining the respective recess 27 formed in the flexible substrate 3.

The vascular graft 1 further comprises a flexible encapsulation layer 51 as shown in FIG. 2. The encapsulation layer 51 is arranged on the first side of the substrate 3 such that, in the rolled-up configuration, the flexible encapsulation layer 51 is arranged radially inward of each of the pressure sensing devices 5, each of the velocity sensing devices 7, and each of the electrically conductive paths 9. The encapsulation layer 51 comprises parylene, preferably a chlorinated parylene, particularly preferred parylene C, and the thickness of the encapsulation layer 51 along the third direction 25 is 1 to 10 µm, preferably 5 µm.

In addition to the vascular graft 1, FIG. 2 shows a flexible processing unit 33 connected via leads 35 to the lead pads 29. The flexible processing unit 33 is configured to process signals received from the vascular graft 1 via the leads 35. The flexible processing unit 33 is attached to the skin 37 of a patient and is adapted to send signals via a wireless interface to a user device 39 with a display 41 on which the user can view information derived from signals provided by the two pressure sensing devices 5 and by the two velocity sensing devices 7 and processed by the flexible processing unit 33.

During a surgical procedure, the vascular graft 1 can be provided in the unrolled configuration as shown in FIG. 1 and can be brought into the rolled-up configuration as shown in FIG. 2. In the rolled-up configuration, the vascular graft 1 can, for example, be connected to two blood vessels such that after the vascular graft 1 is connected to the two blood vessels, the blood flow from one of the two blood vessels is directed through the vascular graft 1 and from the vascular graft 1 to the other one of the two blood vessels. Since in the rolled-up configuration, the first surface 11 of the substrate 3 is facing radially inward, the blood flows along the first surface 11. For example, the blood flows along the axial direction 31. Since the pressure sensing and velocity sensing devices 5, 7 are arranged along the line, which extends along the axial direction 31, the blood passes each of the devices 5, 7 one after the other. The flexible encapsulation layer 51 is arranged radially inward of each of the pressure sensing devices 5, each of the velocity sensing devices 7, and each of the electrically conductive paths 9, and thereby protects each of the pressure sensing devices 5, each of the velocity sensing devices 7, and each of the electrically conductive paths 9 from direct contact with blood.

Depending on the pressure of the blood, particularly the static pressure of the blood, the blood applies a particular mechanical load onto each of the pressure sensing devices 5. The applied mechanical load onto a particular pressure sensing device 5 implies that a mechanical stress is applied to the piezoelectric element 19 of the pressure sensing devices 5 and the mechanical stress applied to the piezoelectric element 19 results in a variation of the electric field extending between the surfaces of the piezoelectric element 19, each surface extends perpendicular to the third direction 25. One of the surfaces of the piezoelectric element 19 is attached to a surface of the first electrode 17 of the pressure sensing device 5 and the other one of the surfaces of the piezoelectric element 19 is attached to a surface of the second electrode 21 of the pressure sensing device 5. Since the first electrode 17 and the second electrode 21 are each coupled to a first end of a respective path 9 and each path 9 is coupled with the second end to the respective lead pad 29, the variation of the electric field due to the applied mechanical load onto each of the pressure sensing devices 5 can be detected from a respective pair of lead pads 29.

The flexible processing unit 33 comprises a charge amplifier 43, a filter 45, a signal processor 47, and a wireless module 49. The flexible processing unit 33 is adapted to process the signals it receives from the lead pads 29 and is adapted to generate signals that comprise information from which the pressure of the blood, particularly the static pressure of the blood, which applies the mechanical load onto a respective pressure sensing device 5, can be inferred. Further, the flexible processing unit 33 is adapted to send the generated signals via the wireless interface to the user device 39. The patient can then view information relating to the pressure of the blood, particularly the static pressure of the blood, displayed on the display 41.

Similarly, depending on the velocity of the blood, the blood applies a particular mechanical load onto each of the velocity sensing devices 7. The cantilever of each velocity sensing device 7 extends from the supported end towards the free end such that the free end is positioned radially inward of a portion of a wall defining the respective recess 27 formed in the substrate 3 and open towards the first side of the substrate 3. Each pair of cantilever and recess 27 is adapted such that blood can enter the recess. Therefore, each cantilever is surrounded by blood from a radially inner side (above the cantilever in FIG. 1 (*b*)) and a radially outer side (below the cantilever in FIG. 1 (*b*), i.e., from the side of the recess 27). Due to the blood flow through the vascular graft 1 and the recess 27, the velocity of the blood at the radially inner side of the cantilever may be higher than the velocity of the blood at the radially outer side of the cantilever. Therefore, the static pressure of the blood at the radially outer side of the cantilever may be higher than the static pressure of the blood at the radially inner side of the cantilever. Therefore, the cantilever may bend towards the radially inner side of the cantilever in case the velocity of the blood at the radially inner side of the cantilever is higher than the velocity of the blood at the radially outer side of the cantilever. The velocity of the blood may vary over time due to the heart muscle pumping blood through the vascular graft 1. For each point in time, depending on the current velocity of the blood, particularly depending on the current difference between the velocity of the blood at the radially inner side of the cantilever and the velocity of the blood at the radially outer side of the cantilever, the blood applies a particular mechanical load onto each of the velocity sensing devices 7, particularly on each of the cantilevers. The applied mechanical load onto a particular velocity sensing device 7 implies that a mechanical stress is applied to the piezoelectric element 19 of the velocity sensing devices 7 and the mechanical stress applied to the piezoelectric element 19 results in a variation of the electric field extending between the surfaces of the piezoelectric element 19, each surface extends perpendicular to the third direction 25. One of the surfaces of the piezoelectric element 19 is attached to a surface of the first electrode 17 of the velocity sensing device 7 and the other one of the surfaces of the piezoelectric element 19 is attached to a surface of the second electrode 21 of the velocity sensing device 7. Since the first electrode 17 and the second electrode 21 are each coupled to a first end of a respective path 9 and each path 9 is coupled with the second end to the respective lead pad 29, the variation of the electric field due to the applied mechanical load onto each of the velocity sensing devices 7 can be detected from a respective pair of lead pads 29.

As already described, the flexible processing unit 33 is adapted to process the signals it receives from the lead pads 29. Further, the flexible processing unit is adapted to generate signals that comprise information from which the velocity of the blood, particularly the difference between the velocity of the blood at the radially inner side of the cantilever and the velocity of the blood at the radially outer side of the cantilever, due to which a particular mechanical load is applied to the respective velocity sensing device 7, can be inferred. Further, the flexible processing unit 33 is adapted to send the generated signals via the wireless interface to the user device 39. The patient can then view information relating to the velocity of the blood, particularly the difference between the velocity of the blood at the radially inner side of the cantilever and the velocity of the blood at the radially outer side of the cantilever, displayed on the display 41.

Therefore, the vascular graft 1 is adapted to provide information from which the pressure and the velocity of the blood can be determined at certain positions in the vascular graft 1. For example, information about the cross section available for the blood to flow through the vascular graft 1 can be derived from the pressure and the velocity of the blood at certain positions in the vascular graft 1. For example, the location, size, and morphology (e.g., shape of a triangle, semi-circle, or rectangle) of a thrombus arranged radially inward of the first surface 11 can be derived.

Figure 3:
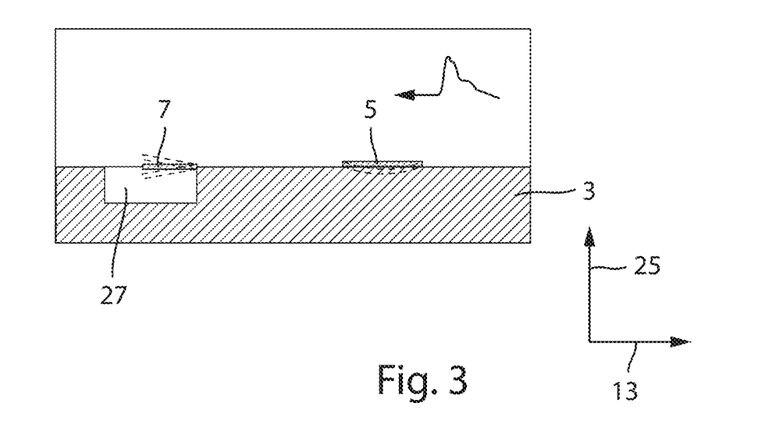

FIG. 3 schematically illustrates a portion of the embodiment of the vascular graft 1 of FIGS. 1 and 2. The direction of the blood flow is symbolized by the arrow. As already described, depending on the pressure of the blood, particularly the static pressure of the blood, the blood applies a particular mechanical load onto the pressure sensing device 5. The applied mechanical load onto the pressure sensing device 5 may deform the pressure sensing device 5, which may assume different deformed configurations, each of which corresponds to a particular pressure of the blood. One deformed configuration of the pressure sensing device 5 is symbolized in FIG. 3 by dashed lines. Since the substrate 3 is flexible, each of the pressure sensing devices 5 can be directly attached to the surface of the substrate 3 and each of the pressure sensing devices 5 can deform together with a portion of the substrate 3, which allows a very compact design of the vascular graft 1.

Similarly, as also already described, depending on the velocity of the blood, particularly depending on the difference between the velocity of the blood at the radially inner side of the cantilever and the velocity of the blood at the radially outer side of the cantilever, the blood applies a particular mechanical load onto the velocity sensing device 7. The applied mechanical load onto the velocity sensing device 7 may deform the velocity sensing device 7, which may assume different deformed configurations, each of which corresponds to a particular velocity of the blood, particularly a particular velocity difference. Two deformed configurations of the velocity sensing device 7 are symbolized in FIG. 3 by dashed lines.

Figure 4:
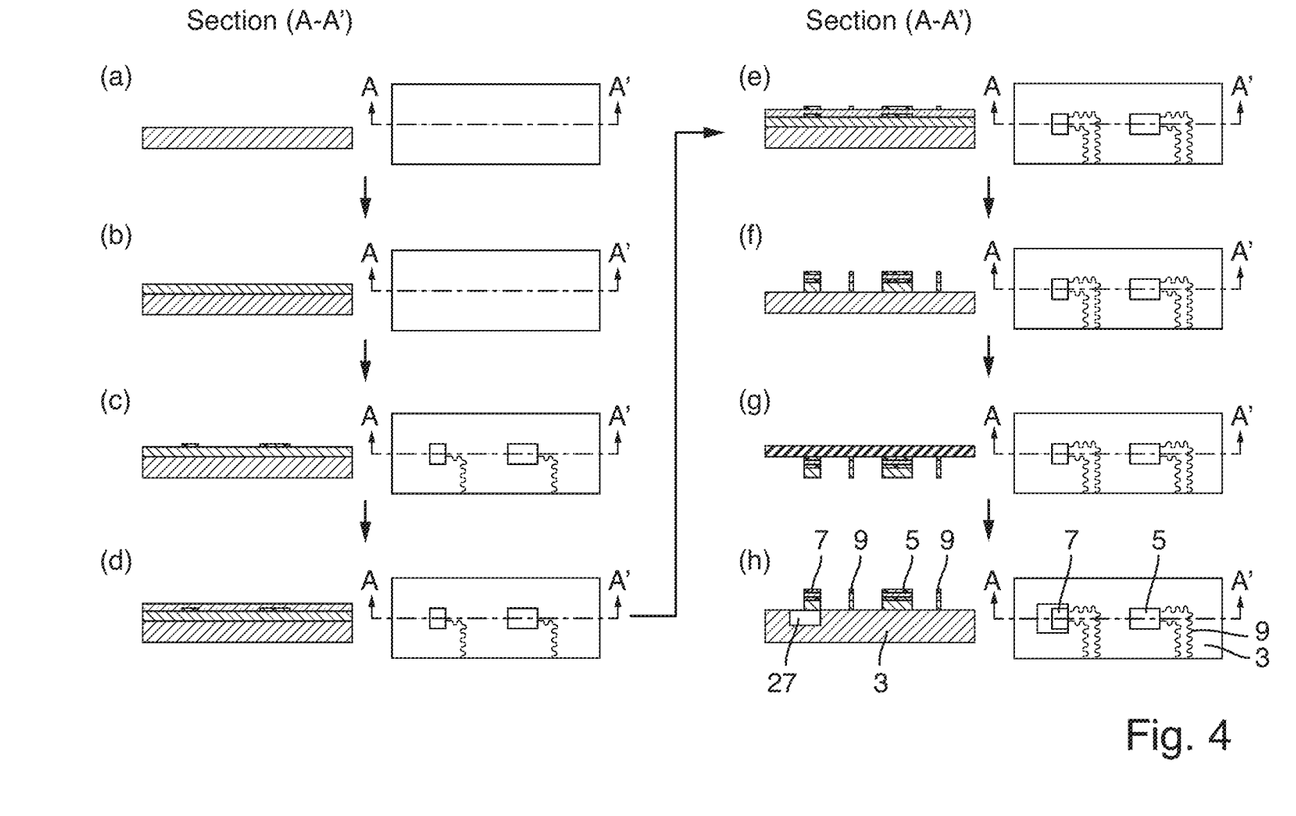

FIG. 4 schematically illustrates a method of manufacturing the vascular graft 1 of FIGS. 1 to 3. The method comprises eight steps (steps (a) to (h)) and for each step a top view is shown on the right side and a sectional view along the line A-A' in the top view is shown on the left side. Particularly, the vascular graft 1 is manufactured with the assistance of techniques to manufacture microelectromechanical systems (MEMS). In step (a), a single-polished silicon wafer is cleaned with acetone and ethyl alcohol. In step (b), Polyimide (PI) is spin-coated on the silicon wafer and heated in a hot oven at 280° C. for 10 min to form a PI film. In step (c), a sputter-coating Au/Cr (160/40 nm) layer is deposited onto the PI film through a shadow mask. In step (d), a piezoelectric PVDF layer is fabricated. The fabrication of the PVDF layer comprises dissolving PVDF powder in dimethylformamide with a weight fraction 15 wt. %. The fabrication of the PVDF layer further comprises exposing the surface of the PI layer fabricated in step (b) and the surface of the Au/Cr layer on the PI layer fabricated in step (c) to oxygen plasma for 60 s before spin-coating of PVDF to increase the interfacial adhesion both between the PI layer and the PVDF layer and between the Au/Cr layer and the PVDF layer. After spin-coating, the PVDF film is heated using a hot plate at 30° C. for 30 min and then annealed at 100° C. for 2 h with a vacuum drying oven to improve the β-phase crystallinity.

In step (e), a sputter-coating Au/Cr (160/40 nm) layer is deposited onto the PVDF layer through a shadow mask. In step (f), the layers deposited on top of the silicon wafer are patterned by a reactive ion etching, RIE, process during which a layer of positive photoresist is employed as a mask. In step (g), water-soluble tapes, WSTs, are used as stamps to pick up the patterned layers. In step (h), a flexible Polydimethylsiloxane, PDMS, substrate is fabricated by a PDMS molding process. Negative molds of the required size of the substrate are fabricated by a rapid prototyping process. The PDMS substrate is peeled out of the molds after PDMS casting. The PDMS substrate is then bonded to the patterned layers. PDMS substrate and the WST are exposed to UV-induced ozone, which creates chemical groups between the patterned layers and the PDMS substrate to enhance bonding strength. The patterned layers are attached to the PDMS substrate and the WST, the patterned layers, and the PDMS substrate are heated in an oven at 70° C. for 10 min, which formed strong bonding between the PDMS substrate and the patterned layers. The WST, the patterned layers, and the PDMS substrate are immersed in water to remove WSTs. An encapsulation layer 51 is formed on top of the patterned layers and the PDMS. A uniform encapsulation layer 51 is formed by employing a vacuum evaporator and a 5 μm thick parylene C encapsulation layer 51 is formed to provide a protection against blood and water and an electrical insulation. A dilute isopropyl alcohol-water solution of organic silane gamma-methacrylxypropyltrimethoxysilane is used before parylene C deposition to improve the adhesion significantly. After the deposition of the encapsulation layer 51, the vascular graft 1 is put on a hot plate at 100° C., and a voltage of 60 V/μm is applied to the lead pads 29 to polarize the piezoelectric PVDF elements 19. After polarization treatment, the lead pads 29 are short-circuited for 24 h.

It is additionally pointed out that "comprising" does not rule out other elements, and "a" or "an" does not rule out a multiplicity. It is also pointed out that features that have been described with reference to one of the above exemplary embodiments may also be disclosed as in combination with other features of other exemplary embodiments described above. Reference signs in the claims are not to be regarded as restrictive.

What is claimed is:

1. A vascular graft, comprising;
    a flexible substrate, which is configured to be an unrolled configuration in which the flexible substrate extends along a main extension plane, and configured to be a rolled-up configuration in which a first surface on a first side of the flexible substrate faces radially inward and a second surface on a second side of the flexible substrate faces radially outward;
    at least one pressure sensing device, which is arranged on the first side of the flexible substrate and comprises a first electrode, a second electrode, and a piezoelectric element arranged between the first electrode and the second electrode;
    at least one velocity sensing device, which is arranged on the first side of the flexible substrate and comprises a first electrode, a second electrode, and a piezoelectric element arranged between the first electrode and the second electrode, wherein said at least one velocity sensing device comprises a cantilever comprising the piezoelectric element of said at least one velocity sensing device; and
    a flexible encapsulation layer, which is arranged on the first side of the flexible substrate in the rolled-up configuration such that the flexible encapsulation layer is positioned over said at least one pressure sensing device, said at least one velocity sensing device, and/or an electrically conductive path in the rolled-up configuration, and arranged radially inward of said at least one pressure sensing device, said at least one velocity sensing device, and/or the electrically conductive path.

2. The vascular graft according to claim 1, wherein the flexible substrate comprises in the unrolled configuration a rectangular shape and in the rolled-up configuration a cylindrical shape.

3. The vascular graft according to claim 1, wherein the flexible substrate comprises Polydimethylsiloxane, PDMS.

4. The vascular graft according to claim 1, wherein each pressure sensing device is formed of a layer stack comprising multiple layers, wherein, when the flexible substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode, the second layer being arranged between the first and the third layers.

5. The vascular graft according to claim 4, wherein a fourth layer of the layer stack comprises a flexible layer arranged between the flexible substrate and the first electrode.

6. The vascular graft according to claim 5, wherein the flexible layer of the pressure sensing device comprises polyimide (PI) and/or the flexible layer of the velocity sensing device comprises polyimide (PI).

7. The vascular graft according to claim 5, wherein the thickness of the flexible layer of the pressure sensing device and/or the thickness of the flexible layer of the velocity sensing device perpendicular to the main extension plane is 2 to 25 μm.

8. The vascular graft according to claim 1, wherein each pressure sensing device comprises in the unrolled configuration a rectangular shape, the rectangular shape comprises an extension along a first direction parallel to the main extension plane of 0.2 to 1.5 mm, and an extension along a second direction parallel to the main extension plane and perpendicular to the first direction of 0.2 to 1 mm.

9. The vascular graft according to claim 1, wherein each pressure sensing device is adapted to detect pressures from 0 to 40 kPa.

10. The vascular graft according to claim 1, wherein, in the unrolled configuration, the cantilever extends from a supported end in parallel to the main extension plane towards a free end such that, in the rolled-up configuration, the free end is positioned radially inward of a portion of a wall defining a recess formed in the flexible substrate, wherein the recess is open towards the first side of the flexible substrate.

11. The vascular graft according to claim 10, wherein the recess comprises in the unrolled configuration a shape of a rectangular cuboid, the rectangular cuboid comprises an extension along a first direction parallel to the main extension plane of 0.5 to 1.5 mm, an extension along a second direction parallel to the main extension plane and perpendicular to the first direction of 0.5 to 1 mm, and an extension along a third direction perpendicular to the main extension plane of 0.2 to 1 mm.

12. The vascular graft according to claim 1, wherein each velocity sensing device is formed of a layer stack comprising multiple layers, wherein, when the flexible substrate is in the unrolled configuration, each layer extends in parallel to the main extension plane, wherein a first layer of the multiple layers comprises the first electrode, a second layer of the multiple layers comprises the piezoelectric element, and a third layer of the multiple layers comprises the second electrode, the second layer being arranged between the first and the third layers.

13. The vascular graft according to claim 12, wherein a fourth layer of the layer stack comprises a flexible layer arranged between the flexible substrate and the first electrode.

14. The vascular graft according to claim 1, wherein each velocity sensing device comprises in the unrolled configuration a square shape, the square shape comprises an extension along a first direction parallel to the main extension plane of 0.2 to 1.5 mm, and an extension along a second direction parallel to the main extension plane and perpendicular to the first direction of 0.2 to 1.5 mm.

15. The vascular graft, according to claim 1, wherein each velocity sensing device is adapted to detect flow velocities from 0 to 1000 ml/min.

16. The vascular graft according to claim 1, wherein the piezoelectric element of the pressure sensing device comprises polyvinylidene difluoride, PVDF, and/or the piezoelectric element of the velocity sensing device comprises polyvinylidene difluoride, PVDF.

17. The vascular graft according to claim 1, wherein the thickness of the piezoelectric element of the pressure sensing device and/or the thickness of the piezoelectric element of the velocity sensing device perpendicular to the main extension plane is 2 to 20 μm.

18. The vascular graft according to claim 1, wherein each pressure sensing device and each velocity sensing device are arranged on the first side of the flexible substrate such that, in the rolled-up configuration, the pressure sensing and velocity sensing devices are arranged along a line, with a distance between the devices along the line of 1 to 10 mm, wherein the line extends along an axial direction of the flexible substrate and is parallel to the axis around which the flexible substrate is rolled up in the rolled-up configuration.

19. The vascular graft according to claim 1, wherein the vascular graft further comprises electrically conductive paths, wherein each of the paths is coupled with one end to one of the elements comprising the first electrode of the pressure sensing device, the second electrode of the pressure sensing device, the first electrode of the velocity sensing device, and the second electrode of the velocity sensing device, wherein each of the paths extends in a meandering shape from the respective first end to a respective second end.

20. The vascular graft according to claim 1, wherein the encapsulation layer comprises parylene.

21. The vascular graft according to claim 1, wherein the thickness of the encapsulation layer perpendicular to the main extension plane is 1 to 10 μm.

22. A vascular graft system comprising the vascular graft according to claim 1 and a flexible processing unit configured to be attachable to a skin and configured to process signals received from the vascular graft.

* * * * *